US011931043B2

(12) United States Patent
Yuasa et al.

(10) Patent No.: US 11,931,043 B2
(45) Date of Patent: Mar. 19, 2024

(54) BENDABLE CLIP DEVICE

(71) Applicant: OLYMPUS MEDICAL SYSTEMS CORP., Tokyo (JP)

(72) Inventors: Masaru Yuasa, Hachioji (JP); Tatsunori Tsuneto, Hino (JP); Shinya Ansai, Koganei (JP); Takushi Haramaki, Fuchu (JP); Shogo Shindo, Koganei (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 17/498,064

(22) Filed: Oct. 11, 2021

(65) Prior Publication Data

US 2022/0117605 A1 Apr. 21, 2022

Related U.S. Application Data

(60) Provisional application No. 63/092,981, filed on Oct. 16, 2020.

(51) Int. Cl.
*A61B 17/122* (2006.01)
*A61B 17/00* (2006.01)
(Continued)

(52) U.S. Cl.
CPC ............ *A61B 17/122* (2013.01); *A61B 17/10* (2013.01); *A61B 17/1285* (2013.01);
(Continued)

(58) Field of Classification Search
CPC . A61B 17/122; A61B 17/1285; A61B 17/083; A61B 17/1227; A61B 17/29;
(Continued)

(56) References Cited

U.S. PATENT DOCUMENTS 5,409,498 A 4/1995 Braddock et al.
5,620,452 A 4/1997 Yoon
(Continued)

FOREIGN PATENT DOCUMENTS

EP 2127606 A1 12/2009
JP 06-209948 A 8/1994
(Continued)

OTHER PUBLICATIONS

Extended European Search Report (OA-1) dated Feb. 11, 2022, issued in corresponding European Patent Application No. 21201423.7.

(Continued)

*Primary Examiner* — Shaun L David
*Assistant Examiner* — Rachael L Geiger
(74) *Attorney, Agent, or Firm* — Morgan, Lewis & Bockius LLP

(57) ABSTRACT

A clip device for gripping biological tissue of a patient includes a clip having a first arm and second arm closeable by operation of a wire that is reciprocally moveable in a longitudinal channel of a sheath; and a bendable member at a distal end region of the sheath. The bendable member can be an integral portion of the sheath or a separate structure. The bendable member is configured to allow a distal end of a clip to rotate or swing toward a proximal end region of the sheath of the device, which orients the clip relative to the sheath to facilitate grasping of tissue even when the approach of the clip is tangential to the tissue, e.g., at an angle (θ) less than 90. The bendable member can be configured to allow a distal end of a clip to rotate or swing toward a proximal end region of a sheath and form an angle of up to at least about 45 degrees, such up to about 60 degrees or up to about 90 degrees, or higher.

19 Claims, 10 Drawing Sheets

80 85a 85 86a 88 86b 87 81 84 S1 S2 S3 87a 87 86b 85 87a 88 86a 84 81

(51) Int. Cl.

| | |
|---|---|
| ***A61B 17/08*** | (2006.01) |
| ***A61B 17/10*** | (2006.01) |
| ***A61B 17/128*** | (2006.01) |

(52) U.S. Cl.

CPC ............... *A61B 2017/00336* (2013.01); *A61B 2017/0034* (2013.01); *A61B 2017/00367* (2013.01); *A61B 2017/00831* (2013.01); *A61B 17/083* (2013.01)

(58) Field of Classification Search

CPC .. A61B 2017/00336; A61B 2017/0033; A61B 2017/0034; A61B 2017/00367; A61B 2017/00831; A61B 2017/00964; A61B 2017/12004; A61B 2017/2926

See application file for complete search history.

(56) References Cited

U.S. PATENT DOCUMENTS

| | | | | |
|---|---|---|---|---|
| 8,162,959 | B2 | 4/2012 | Cohen et al. | |
| 8,480,685 | B2 | 7/2013 | Kimura et al. | |
| 9,949,740 | B2 | 4/2018 | Satake et al. | |
| 10,624,642 | B2 | 4/2020 | Randhawa | |
| 10,786,254 | B2 | 9/2020 | Wells et al. | |
| 2002/0045909 | A1 | 4/2002 | Kimura et al. | |
| 2002/0138086 | A1 | 9/2002 | Sixto et al. | |
| 2002/0165560 | A1 | 11/2002 | Panitz et al. | |
| 2002/0198541 | A1 * | 12/2002 | Smith ................ | A61B 17/1285 606/142 |
| 2004/0176784 | A1 * | 9/2004 | Okada ................ | A61B 17/1285 606/151 |
| 2005/0059985 | A1 | 3/2005 | Kimura | |
| 2005/0143767 | A1 | 6/2005 | Kimura et al. | |
| 2006/0271066 | A1 | 11/2006 | Kimura et al. | |
| 2006/0276775 | A1 * | 12/2006 | Rosenberg ......... | A61B 17/0469 606/1 |
| 2008/0114377 | A1 * | 5/2008 | Shibata ............. | A61B 17/1285 606/142 |
| 2009/0318937 | A1 | 12/2009 | Matsuoka et al. | |
| 2010/0152753 | A1 | 6/2010 | Menn et al. | |
| 2011/0172682 | A1 | 7/2011 | Brady et al. | |
| 2011/0208211 | A1 | 8/2011 | Whitfield et al. | |
| 2011/0319710 | A1 | 12/2011 | Phillips-Hungerford et al. | |
| 2012/0029534 | A1 | 2/2012 | Whitfield et al. | |
| 2012/0150301 | A1 * | 6/2012 | Gamache ............. | A61B 17/808 606/104 |
| 2013/0023925 | A1 * | 1/2013 | Mueller ................. | A61B 17/29 606/205 |
| 2013/0158566 | A1 | 6/2013 | Harris et al. | |
| 2013/0310857 | A1 | 11/2013 | Iceman et al. | |
| 2015/0133969 | A1 | 5/2015 | Gupta et al. | |
| 2017/0340443 | A1 * | 11/2017 | Stearns .............. | A61B 17/0401 |
| 2019/0150929 | A1 | 5/2019 | Gregan et al. | |
| 2019/0321047 | A1 | 10/2019 | Thomas et al. | |
| 2020/0113616 | A1 | 4/2020 | Honda | |
| 2020/0205836 | A1 * | 7/2020 | Uesaka .............. | A61B 17/1285 |
| 2021/0106335 | A1 | 4/2021 | Sugitani et al. | |

FOREIGN PATENT DOCUMENTS

| | | | |
|---|---|---|---|
| JP | 2004-121485 | A | 4/2004 |
| JP | 2004-527312 | A | 9/2004 |
| JP | 2005-058626 | A | 3/2005 |
| JP | 2006-158668 | A | 6/2006 |
| JP | 2007-097664 | A | 4/2007 |
| JP | 2007-136128 | A | 6/2007 |
| JP | 2008-119068 | A | 5/2008 |
| JP | 2010-213990 | A | 9/2010 |
| JP | 2011-172931 | A | 9/2011 |
| JP | 2012-030070 | A | 2/2012 |
| JP | 2015-008858 | A | 1/2015 |
| JP | 2017-192513 | A | 10/2017 |
| JP | 2018-061672 | A | 4/2018 |
| WO | 2002/087421 | A2 | 11/2002 |
| WO | 2012/039163 | A1 | 3/2012 |
| WO | 2019/099698 | A1 | 5/2019 |
| WO | 2019/189864 | A1 | 10/2019 |
| WO | 2019/207585 | A1 | 10/2019 |
| WO | 2020/136906 | A1 | 7/2020 |
| WO | 2020/189666 | A1 | 9/2020 |

OTHER PUBLICATIONS

Extended European Search Report (OA-2) dated Mar. 11, 2022, issued in corresponding European Patent Application No. 21201671.1.

Office Action (OA-1) dated Sep. 6, 2022, issued in corresponding Japanese Patent Application No. 2021-165768.

Office Action (OA-2) dated Sep. 6, 2022, issued in corresponding Japanese Patent Application No. 2021-165771.

Office Action dated Jul. 5, 2023 in U.S. Appl. No. 17/498,062.

Office Action dated Mar. 15, 2023, issued in related U.S. Appl. No. 17/498,062.

International Search Report dated Jan. 11, 2022, issued in corresponding International Search Report PCT/JP2021/038151.

Office Action dated Nov. 15, 2023, issued in Chinese Patent Application No. 202111181510.X.

Office Action dated Jan. 4, 2024, issued in U.S. Appl. No. 17/498,062.

* cited by examiner

BENDABLE CLIP DEVICE

CROSS-REFERENCE TO RELATED APPLICATION

This application claims the benefit of U.S. Provisional Application No. 63/092,981 filed 16 Oct. 2020, the entire disclosure of which is hereby incorporated by reference herein.

TECHNICAL FIELD

The present invention relates to a clip device for gripping tissue of a patient that includes a clip, a sheath and a bendable member that can rotate the clip toward the sheath.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

Endoscopic clips, i.e., endoclips, are surgical tools used with endoscopes that can grasp tissue within a human body. Endoclips have found use in therapeutic procedures such as to prevent tissue bleeding, closing perforations, and other surgical procedures. There are many types of endoclips differing in shape and/or size, which can be administered using single use and reloadable systems, and may or may not open and close to facilitate placement of the clip in the body.

U.S. Patent Publication Number 2013/158566 discloses a rotational mechanism for endoscopic devices that permits rotation of a clip during insertion of the clip to a target site in a living body. The patent publication discloses endoscopic devices that include a rotation drive with several rigid components to effect a limited rotation of the clip.

However, a continuing need exists for clip devices configured to grasp tissue of a patient in a surgical procedure.

SUMMARY OF THE DISCLOSURE

An advantage of the present invention is a clip device for gripping biological tissue of a patient that includes a sheath having a bendable member at a distal end region that can rotate the clip to facilitate grasping the tissue, particularly when the clip does not approach the tissue at a vertical direction. Advantageously, the bendable member does not need actuators or wires to rotate the clip but rather is configured to rotate the clip by applying pressure to the clip during use.

These and other advantages are satisfied, at least in part, by a clip device comprising a clip having a first arm and second arm in which the first arm and second arm are configured to move in a direction toward each other to close the clip; a sheath having a longitudinal channel in which a wire connected to a proximal end of the clip can reciprocally move within the longitudinal channel of the sheath to operate the clip; wherein the sheath includes a bendable member at a distal end region of the sheath and aligned with the longitudinal channel of the sheath. The bendable member is configured to allow a distal end of the clip to swing toward a proximal end region of the sheath. Advantageously, the bendable member can be configured to rotate the distal end of the clip to the proximal end region of the sheath at an angle of up to at least about 45 degrees, such up to about 60 degrees or up to about 90 degrees, or higher. The bendable member can comprise a flexible tube connected or extending from a distal end region of the sheath or the bendable member can be an integral portion of the sheath itself, in which a proximal end region is more rigid that the distal end region, or the bendable member can comprise a joint connected along the distal end region of the sheath, etc.

Embodiments of the present disclosure include one or more of the following features individually or combined. For example, the bendable member can comprise metal or polymeric materials (e.g., stainless-steel, an elastomer, a fluorinated polyolefin such as polytetrafluoroethylene, a polyolefin such as polyethylene). In an aspect of the present disclosure, a sheath can be such as by heat treatment or by covering with a rigid tube to make the proximal end region of the sheath more rigid than a distal end region of the sheath. In other aspects, the bendable member is can be joined to the sheath by an adhesive or weld.

In other aspects, the clip device can include a connection member connecting the proximal end of the clip and a distal end of the wire and slibaly movable within the longitudinal channel of the sheath. In some embodiments, the distal end of the bendable member does not overlap the distal end of the wire connected to the connection member when the clip is in a closed state. In other embodiments, the connection member comprises a joint having an articulating distal part and proximal part joined by a pin. In still further embodiments, the connection member can rotate within the bendable member. In additional embodiments, the connection member has a tapered proximal end connected to the distal end of the wire. In other aspects, the clip device can include a segmental member reciprocally movable over the bendable member to lock the bendable member from rotating.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein.

Figure 1:
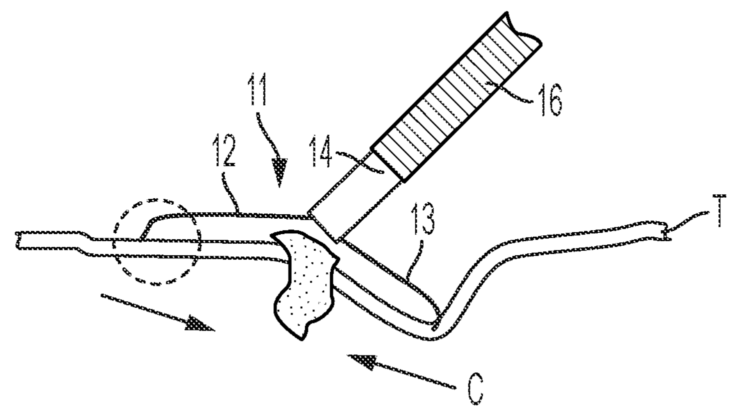
FIG. 1 schematically illustrates a clip device without a bendable member.

Throughout all of the drawings, dimensions of respective constituent elements are appropriately adjusted for clarity. For ease of viewing, in some instances only some of the named features in the figures are labeled with reference numerals.

DETAILED DESCRIPTION OF THE DISCLOSURE

The present disclosure is directed to clip devices that are useful in therapeutic procedures of a patient such as to prevent tissue bleeding, closing perforations and hemostasis, and suture contraction of the inner wound, marking lesions and traction (mucosal elevation) and other surgical procedures. The term "patient," as used herein, comprises any and all organisms and includes the term "subject." A patient can be a human or an animal.

Generally a clip device for grasping tissue of a patient includes a clip that can be actuated by a wire configured in a sheath in which the wire can advance and retract longitudinally by operating a handle of the device. References herein to the term "distal" are to a direction away from the operating handle, while references to the term "proximal" are to a direction towards the operating handle.

FIG. 1 schematically illustrates a conventional clip device. As shown, such a device includes a clip 10 having arms 12, 13, for grasping tissue (T). The device further includes a pressing pipe 14 connected to a sheath 16. As further illustrated, when such a conventional device approaches tissue at an angle (θ) less than 90 (less than a perpendicular approach, such as a tangential approach) the arms may slip when closing the clip (C) and thus grasping the tissue becomes difficult. In particular, the arm furthest from the tissue (arm 12) can slip since there is less pressure applied on the second arm during a tangential approach to tissue.

However, a clip device of the present disclosure advantageously includes a sheath having a bendable member at a distal end region of the sheath which can orient the clip relative to a proximal end region of the sheath to facilitate grasping of tissue. Such a bendable member is a structural feature configured to allow a distal end of a clip to rotate or swing toward a proximal end region of a sheath of the device. In moving toward the proximal end of the sheath of the device, the distal end of a clip is moved to a position that is closer to the proximal end of the sheath of the device. The bendable member is configured preferably such that a distal end of the clip can rotate or swing toward a proximal end of a sheath to form an angle of up to at least about 45 degrees, such up to about 60 degrees, or up to about 90 degrees, or higher. Bendable members useful for the clip devices of the present disclosure include, for example, a flexible tube extending from a distal end of the sheath, or a flexible tube connected to a distal end region of the sheath, or a joint along a distal end region of the sheath, etc.

A bendable member of the present disclosure can comprise metal or polymeric materials (e.g., stainless-steel, an elastomer, a fluorinated polyolefin such as polytetrafluoroethylene, a polyolefin such as polyethylene). The bendable member can be an integral portion of the sheath at a distal end region thereof or can be a separate part joined to the sheath by an adhesive or weld. The bendable member at a distal end region of the sheath is configured to be more flexible than a proximal region of the sheath, which can be achieved by choice of materials for the respective bendable member and sheath, differences in designs or thicknesses, treating or not treating the respective regions of the sheath, covering a proximal end region, etc., or combinations thereof. Advantageously, the bendable member can be actuated by applying pressure to the distal end of the clip through the sheath which causes the bendable member to rotate the distal end of the clip to a proximal end of the sheath.

In certain aspects, it is advantageous to have the bendable member close to the proximal end of the clip so that the distance between the tissue and sheath can be minimized. In certain embodiments, the proximal end of the flexible member is no further than about 100 mm to the proximal end of the clip. In other embodiments, the bendable member has a length from a distal end to a proximal end of no greater than about 90 mm, such as no greater than about 80 mm, 70 mm, 60 mm, 50 mm, 40 mm, 30 mm, 20 mm, 10 mm and values therebetween.

Various aspects of a clip device according to the present disclosure will be described with references to FIGS. 2 through 12.

Figure 2A:
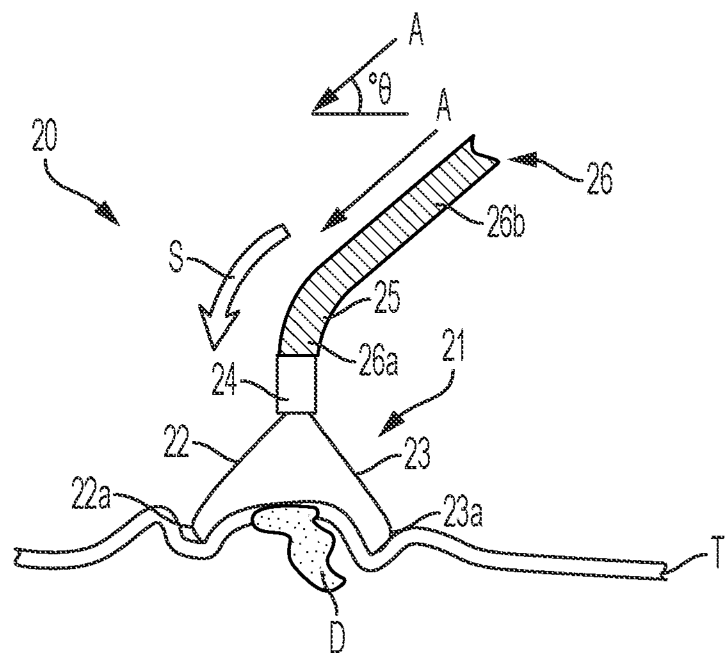
FIGS. 2A and 2B schematically illustrate a clip device with a sheath including a bendable member in accordance with aspects of the present disclosure.
Figure 2B:
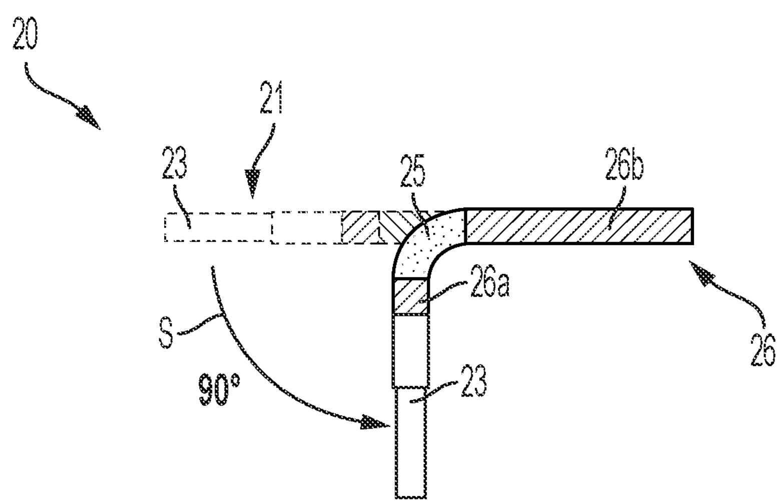

FIGS. 2A and 2B schematically illustrate a clip device with a sheath including a bendable member in accordance with aspects of the present disclosure. As illustrated, the device 20 includes a clip 21, having a first arm 22 and second arm 23, and a sheath 26, which can be in the form of a tube, coil, etc. The first arm 22 and second arm 23 are configured to move in a direction toward each other to close the clip 21 by operation of a wire connected to a proximal end of the clip (not shown). For this example, first arm 22 includes first claw **22*a* and second arm 23 includes second claw 23*a* and sheath 26 is connected to a pressing pipe 24. Sheath 26 has a longitudinal channel (not shown) and the wire can reciprocally move within the longitudinal channel of the sheath to operate the clip. The wire (not shown) can be connected to the proximal end of the clip 21 and the opposite end of the wire can be connected to an operating handle (not shown) which can cause the clip 21** to reciprocally move from the pressing pipe to open or close the clip.

As further illustrated in FIG. 2A, sheath 26 includes a bendable member 25 at a distal end region of the sheath along the longitudinal channel of the sheath that can cause the clip to swing (S) toward a proximal end of the sheath with an applied force when operating the device. For this example, bendable member 25 is between a distal end region 26*a* of sheath 26 to a proximal end region 26*b* of sheath 26. An advantage of clip devices of the present disclosure is that the clip 21 can grasp tissue even when the original approach (A) of the clip is tangential to the tissue (T), e.g., at an angle (θ) less than 90 as shown in FIG. 2A.

FIG. 2B schematically illustrates a side view of the sheath with bendable member of clip device 20 shown in FIG. 2A. As further shown in FIG. 2B, bendable member 25 is between distal end region 26*a* and proximal end region 26*b* of sheath 26 along the longitudinal channel of sheath 26 and is configured to rotate a distal end of clip 21 to swing toward a proximal end of the sheath. Advantageously, the bendable member of the present disclosure allows a distal end of the clip to form up to a 90 degree angle relative to a proximal end of the sheath (FIG. 2B). As shown by FIGS. 2A and 2B, when the clip approaches tissue tangentially, the bendable member 25 can allow a distal end of the clip to swing toward a proximal end of the sheath so that the clip 21 is in a more vertical direction to the tissue (T) near a defect (D). Such a relative position of the clip and tissue can more readily elevate the tissue so that the claws of the arms of the clip can more readily grasp the tissue.

The bendable member as illustrated in FIGS. 2A and 2B can be an integral part of the sheath or can comprise a flexible tube connected to the sheath and joined to the sheath by an adhesive or weld. The bendable member can be made of a metal such as stainless-steel, an elastomer, a polyolefin such as a fluorinated polyolefin, etc. provided that the bendable member (e.g., flexible tube) is configured to be more flexible than the proximal end region of the sheath. Increasing flexibility of the bendable member relative to the proximal end region of the sheath can be done by choice of materials for the respective bendable member and sheath, differences in design or thicknesses, treating the proximal end region, etc., or combinations thereof.

Figure 3:
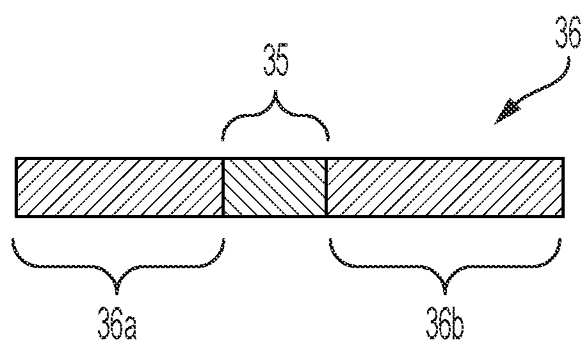
FIG. 3 schematically illustrates an embodiment of a bendable member in the form of a flexible tube in accordance with aspects of the present disclosure.
Figure 4:
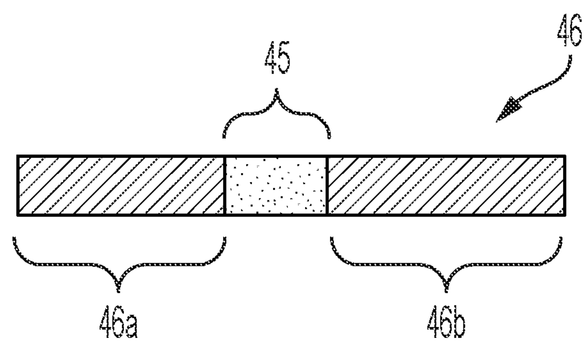
FIG. 4 schematically illustrates another embodiment of a bendable member comprised of a flexible tube in accordance with aspects of the present disclosure.

FIGS. 3-5 schematically illustrate certain aspects of a bendable member and sheath of a clip device of the present disclosure. In particular, FIG. 3 shows a bendable member 35 in the form of a flexible tube connected along the longitudinal channel of the sheath between a distal end region 36*a* and proximal end region 36*b* of sheath 36. In this example, bendable member 35 is made of a metal configured to have higher flexibility than sheath 36, which can be composed of a metal. The sheath can be in the form of a continuous tube or a coil provided the sheath is stiffer than the bendable member. The bendable member 35 can be connected to the sheath by welding with an adhesive.

FIG. 4 shows a bendable member 45 comprised of a flexible tube connected between a distal end region 46*a* and proximal end region 46*b* of sheath 46 and along the longitudinal channel of the sheath. In this example, bendable member 45 is made of a polymeric resin such as an elastomeric material and configured to have higher flexibility than the sheath, which can be composed of a metal. The sheath can be in the form of a continuous tube or a coil provided the sheath is stiffer than the bendable member. The bendable member can be connected to the sheath by an adhesive.

Figure 5A:
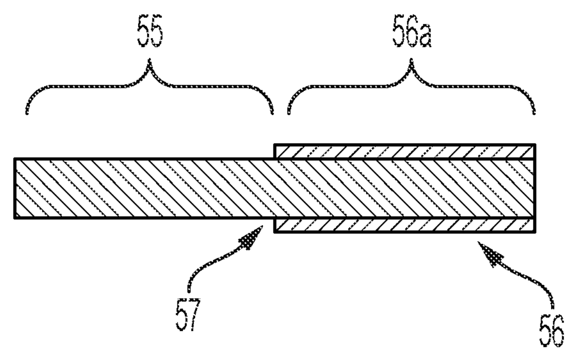
FIG. 5A schematically illustrates another embodiment of a bendable member in the form of a tube extending from a distal end of a sheath in accordance with aspects of the present disclosure.

FIG. 5A shows bendable member comprised of a flexible tube 55 inserted into distal end region 56*a* of a sheath 56 and extending from a distal opening 57 of the distal end region 56*a*. Flexible tube 55 can be made of a metal or polymeric material and configured to be more flexible than sheath 56. As further illustrated in FIG. 5A, the distal opening 57 of the distal end 56*a* of sheath 56, which contacts a proximal end region of the flexible tube 55, acts as a fulcrum to apply pressure to the flexible tube facilitating bending of the flexible tube at the distal opening 57. In this example, flexible tube 55 extends proximally inside sheath 56.

In another aspect of the present disclosure, a bendable member can be an integral portion of the sheath. For example, heat treating a distal end region of a sheath can make the distal region relatively more flexible than an untreated proximal end region thereby forming a sheath with a bendable member at the distal end region. Such heat treatment can be carried out in a manner to form a bendable member between rigid portions of the sheath to yield a structure as shown in FIGS. 3-4 except the bendable member is a heat treated portion of the sheath rather than a separate tube connected to the sheath.

Figure 5B:
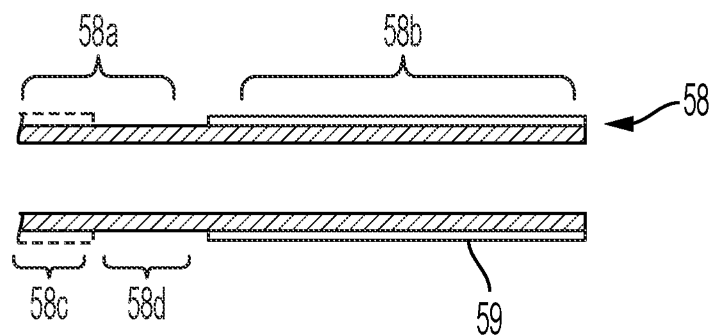
FIG. 5B schematically illustrates a sheath including a bendable member as an integral portion of the sheath.

Alternatively, a bendable member can be an integral portion of the sheath by covering an outer periphery of a proximal end region of a bendable sheath with a tube (for example, a heat shrinkable tube) to make the proximal end region of the sheath rigid while maintaining the bendability of a distal end region of the sheath. FIG. 5B schematically illustrates a sheath including a bendable member as an integral portion of the sheath. As shown in the figure, sheath 58 includes a bendable member 58*a* at a distal end region of sheath 58 and a rigid proximal end region 58*b* as an integral sheath. Proximal end region 58*b* of sheath 58 can be covered by a rigid tube 59 (e.g., a heat shrinkable tube) such that the proximal end region 58*b* of sheath 58 is rigid while the distal end region 58*a* of sheath 58 remains bendable. An additional optional aspect of this example includes covering a distal end region of sheath 58 to form a rigid distal end region 58*c* of sheath 58. (The rigid distal end region 58*c* of sheath 58 is illustrated as a dashed line on sheath 58 to indicate it is an optional element, e.g., without a rigid distal end region 58*c*, the bendable member is 58*a* and with the optional rigid distal end region 58*c*, the bendable member is 58*d*.) By including a rigid distal end region 58*c*, a bendable member 58*d* can be formed between the distal end region 58*c* and proximal end region 58*b* of the sheath.

The bendable members schematically illustrated in FIGS. 2-5 advantageously include flexible elements to a sheath for bendability without interconnected moving parts. The bendable members schematically illustrated in FIGS. 2-5 are further relatively straight forward to manufacture and can be inserted in conventional channels of endoscopes.

Figure 6:
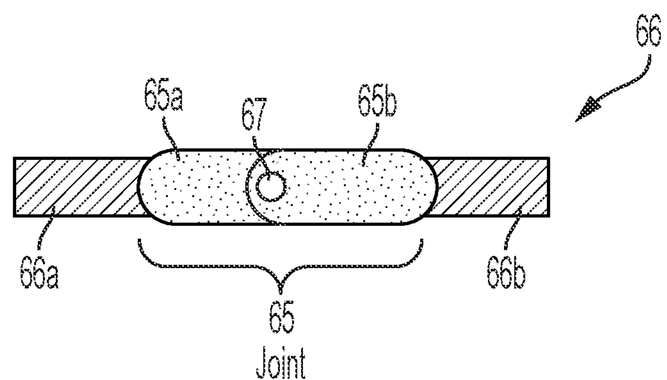
FIG. 6 schematically illustrates a sheath including a bendable member composed of a joint having articulating distal and proximal parts joined by a pin in accordance with aspects of the present disclosure.

FIG. 6 shows another embodiment of a bendable member that can be connected along the longitudinal channel of the sheath. In this example, bendable member 65 is articulated and is composed of a joint having a distal part 65*a* and proximal part 65*b* joined by, e.g., a pin to form the joint along the longitudinal channel of the sheath 66. The articulating distal part and proximal part of the joint can comprise distal and proximal tubes connected by a pin and attached to the distal and proximal ends of the sheath. In this example, bendable member 65 can be composed of metal or polymeric material and the sheath can be in the form of a continuous tube or a coil. The bendable member can be connected along the longitudinal channel of the sheath by welds or by an adhesive.

Figure 7:
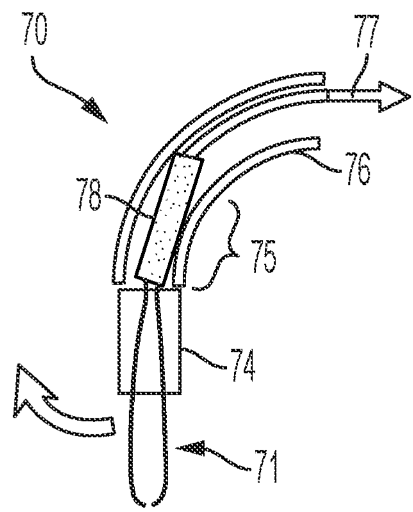
FIG. 7 schematically illustrates implementing a bendable member in a clip device in accordance with aspects of the present disclosure.

FIGS. 7-12 schematically illustrate certain aspects of implementing a bendable member in a clip device of the present disclosure. In particular, FIG. 7 shows a clip device 70 for gripping biological tissue of a patient comprised of a clip 71 having arms with claws, a pressing pipe 74 connected to a sheath 76 having a longitudinal channel and a wire 77 that can reciprocally move within the longitudinal channel of the sheath. A bendable member 75 is connected to a distal end region of the sheath along the longitudinal channel of the sheath. In this example, the wire 77 is connected to a proximal end of the clip 71 by a connection member 78.

In operation, a handle (not shown) connected to a proximal end of the wire operates the wire to retract the clip in a pressing pipe to close the clip arms. Certain clip devices can include a link mechanism that can engage and release a pressing tube from the sheath. Such devices include a connection member to engage and disengage a distal end of the clip from the wire. In addition, the connection member can include internal engaging and disengaging elements. Such clip devices are disclosed in international patent application number WO 2020/136906, which is incorporated herein by reference hereby.

However, the additional components of a clip device that includes a connection member to engage and disengage the clip can interfere with the bendable member when a distal end of a clip swings toward a proximal end of the sheath at a high angle, e.g., at an angle greater than about 60 degrees, such as up to about 90 degrees or greater.

Figure 8:
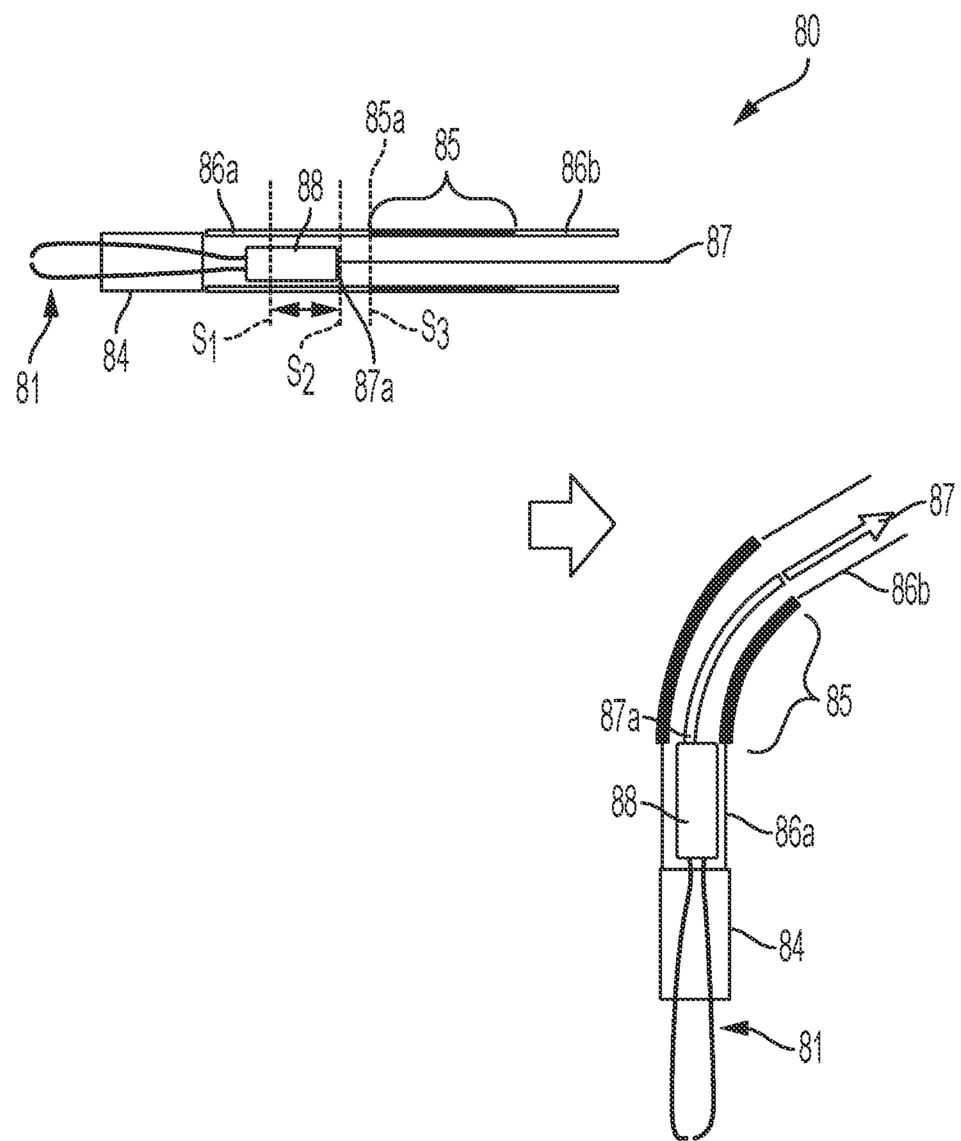
FIG. 8 schematically illustrates another implementation of a bendable member in a clip device in which the distal end of the bendable member is proximal to a distal end of a wire when the clip is in a closed state.

FIG. 8 schematically illustrates another implementation of a bendable member in a clip device and, in particular, this figure illustrates a bendable member located along the sheath at a distance from a connection member such that the connection member does not move within the longitudinal channel of the bendable member. As shown, a clip device 80 includes a clip 81 having arms with claws, which is shown in a closed state. The device is illustrated to further include a pressing pipe 84 connected to a distal end region 86*a* of a sheath 86, which has a longitudinal channel in which a wire 87 can reciprocally move. A bendable member 85 is connected between distal end region 86*a* and proximal end region 86*b* of the sheath 86 along the longitudinal channel of the sheath.

In this example, connection member 88 is between a proximal end of the clip 81 and a distal end 87*a* of the wire 87 and can slibaly move within the longitudinal channel of the sheath. The connection member can connect the proximal end of clip 81 and distal end 87*a* of the wire 87 directly or through interrelated elements (not shown) that are configured to release the clip. FIG. 8 further illustrates a sliding length range (e.g., between S1 and S2) for the distal end 87*a* of the wire 87 between a distal location (S1) and proximal location (S2) along the longitudinal channel of the sheath. The sliding length range (S1 and S2) will depend on the distal and proximal length needed for the clip to travel to open and close the clip when operating the device, which can be predetermined. The distal location (S1) of the range that the distal end 87*a* of the wire travels in the longitudinal channel represents the clip in the open state and the proximal location (S2) of the range that the distal end 87*a* of the wire travels represents the clip in the closed state. As shown in this figure, the distal end region 85*a* of the bendable member does not overlap the proximal location (S2) that the distal end 87*a* of wire travels when the clip is in a closed state. Thus, for this example, the distal end of the bendable member is proximal to a distal end of a wire when the clip is in a closed state.

Figure 9:
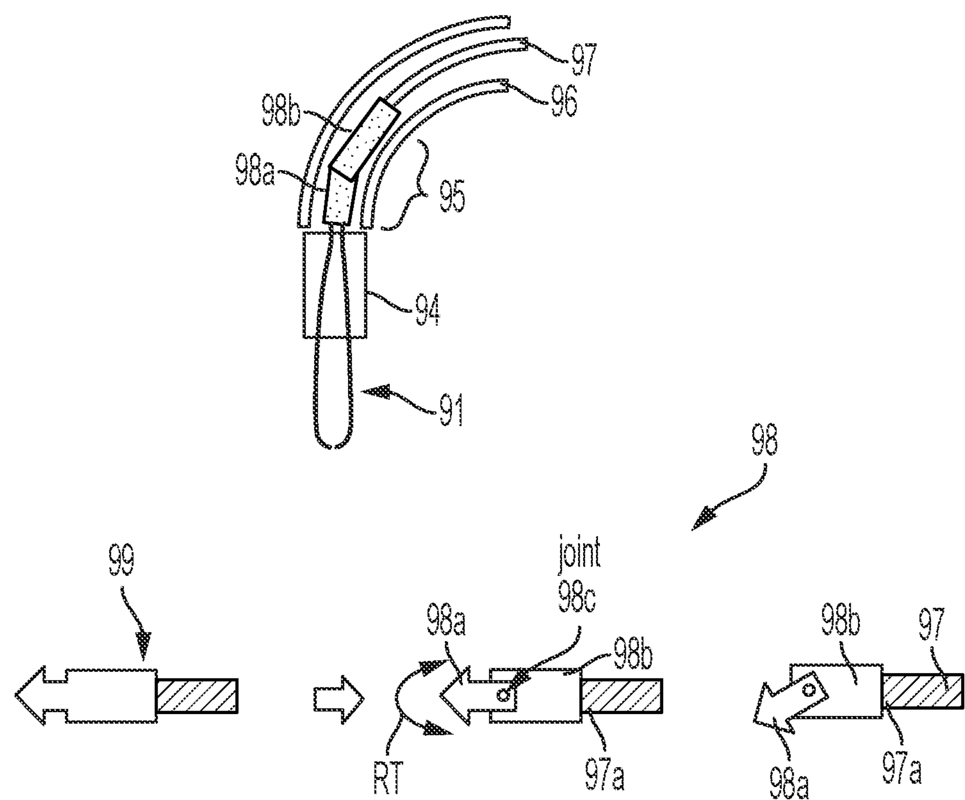
FIG. 9 schematically illustrates another implementation of a bendable member in a clip device in which a connection member is comprised of a joint having articulating distal and proximal parts joined by a pin.
Figure 10:
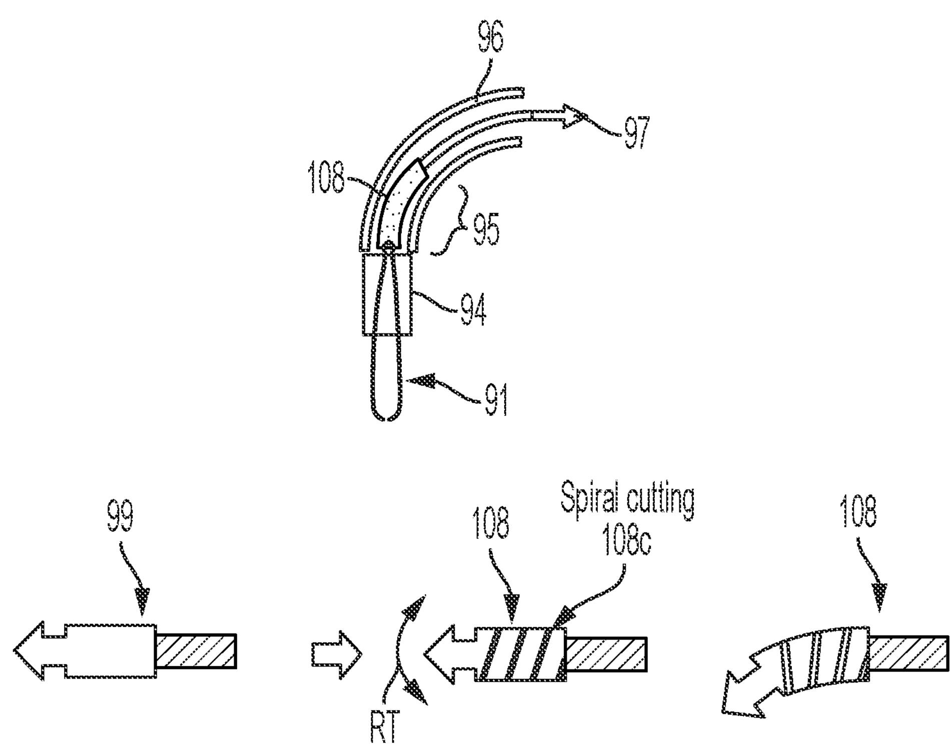
FIG. 10 schematically illustrates another implementation of a bendable member in a clip device in which a connection member, connecting a proximal end of a clip to a wire, is configured to rotate.

FIGS. 9 and 10 schematically illustrate other implementations of a bendable member in a clip device of the present disclosure. As shown in FIGS. 9-10, a clip device includes a clip 91 having arms with claws, a pressing pipe 94 connected to a distal end of a sheath 96, which has a longitudinal channel, and a wire 97 that can reciprocally move within the longitudinal channel of the sheath. A bendable member 95 is connected at the distal end region of the sheath 96 and along the longitudinal channel of the sheath.

In FIG. 9, connection member 98, between a proximal end of the clip 91 and distal end 97*a* of wire 97, includes two articulating parts (98*a*, 98*b*) connected by a pin (98*c*) to form a joint. As illustrated, the connection member 98 is slibaly movable within the longitudinal channel of the sheath and can slidable move within a longitudinal channel of the bendable member 95. The connection member 98 can connect the proximal end of clip 91 and distal end 97*a* of the wire 97 directly or through interrelated elements (not shown) that are configured to release the clip. In one embodiment, connection member 99 is configured to engage and disengage a proximal end of the clip. In another embodiment, a connection member such as 99 can be configured to rotate and bend due to the joint, e.g., connection member 98. As shown in FIG. 9, connection member 98 is comprised of a joint having an articulating distal part 98*a* and proximal part 98*b* joined by a pin 98*c*. Although FIG. 9 illustrates articulating distal part 98*a* and proximal part 98*b* joined by a separate pin 98*c*, the articulating distal part 98*a* and proximal part 98*b* can be alternatively integrated as a whole part. Configuring connection member with a joint allows the distal part to rotate (RT) so that such a connection member minimizes interference with the bendable member when the connection member extends into the longitudinal channel of the bendable member and the bendable member is rotated as shown in FIG. 9.

In FIG. 10, connection member 108, between a proximal end of the clip 91 and distal end of wire 97, is configured to rotate (RT). Connection member 108 can be configured to rotate by choice of materials, e.g., a flexible plastic or by designed such as including a spiral cut along an outer surface of the member, etc. or combinations thereof. As illustrated in FIG. 10, the connection member 108 is slibaly movable within the longitudinal channel of the sheath and can slidably move within a longitudinal channel of the bendable member 95. The connection member can connect the proximal end of clip 91 and distal end of the wire 97 directly or through interrelated elements (not shown) that are configured to release the clip. In one embodiment, a connection member such as 99 can be configured to rotate within the bendable member, e.g., connection member 108, as shown in FIG. 10. Such a rotatable connection member can minimize interference with the bendable member when the connection member extends into the longitudinal channel of the bendable member and the bendable member is rotated as shown in FIG. 10.

Figure 11:
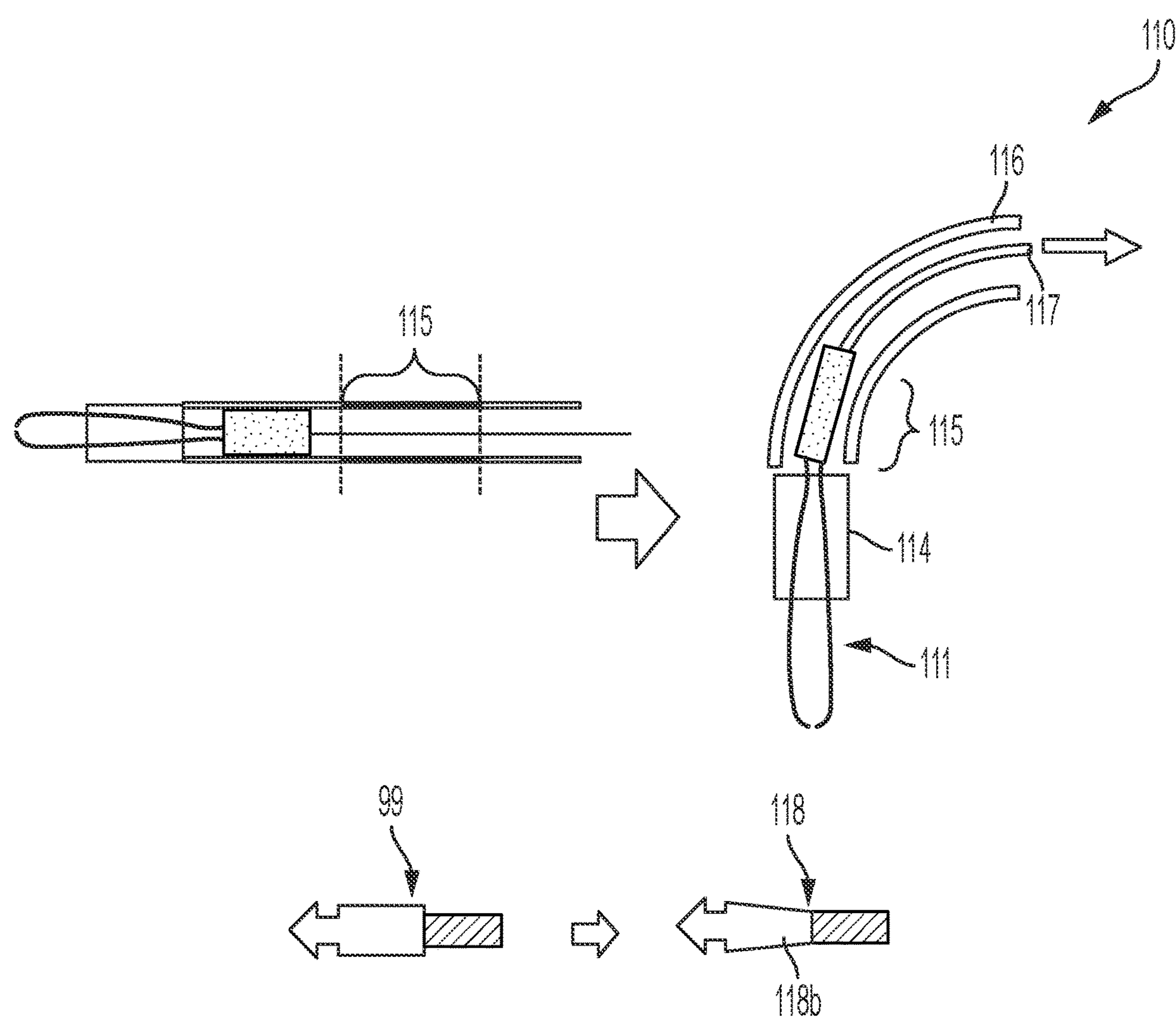
FIG. 11 schematically illustrates another implementation of a bendable member in a clip device in which a connection member, connecting a proximal end of a clip to a wire, has a tapered proximal connected to the wire.

FIG. 11 shows another implementation of a clip device with a bendable member in accordance with the present disclosure. As shown, a clip device 110 includes a clip 111 having arms with claws, which is shown in a closed state. The device is illustrated to further include a pressing pipe 114 connected to a distal end of a sheath 116, which has a longitudinal channel in which a wire 117 can reciprocally move. A bendable member 115 is connected at a distal end region of the sheath 116 along the longitudinal channel of the sheath.

In FIG. 11, connection member 118, between a proximal end of the clip 111 and distal end of wire 117, is configured to have a tapered proximal end 118*b* connected to the distal end of wire 117. As illustrated in FIG. 11, the connection member 118 is slibaly movable within the longitudinal channel of the sheath and can slidably extend into a longitudinal channel of the bendable member 115. The connection member can connect the proximal end of clip 111 and distal end of the wire 117 directly or through interrelated elements (not shown) that are configured to release the clip. Connection member 99 is configured to engage and disengage a proximal end of the clip. Connection member 118 is also configured to engage and disengage a proximal end of the clip but the tapered proximal end 118*b* of connection member 118 can minimize interference with the bendable member when the connection member extends into the bendable member and the bendable member is rotated.

In certain operations, it may be advantageous to lock the bendable member from rotating. When the need arises, the bendable member can be unlocked to rotate or swing the clip toward a proximal end of the sheath. Such a locking mechanism can be implemented by a segmental member reciprocally movable over the bendable member to lock the bendable member from rotating.

Figure 12A:
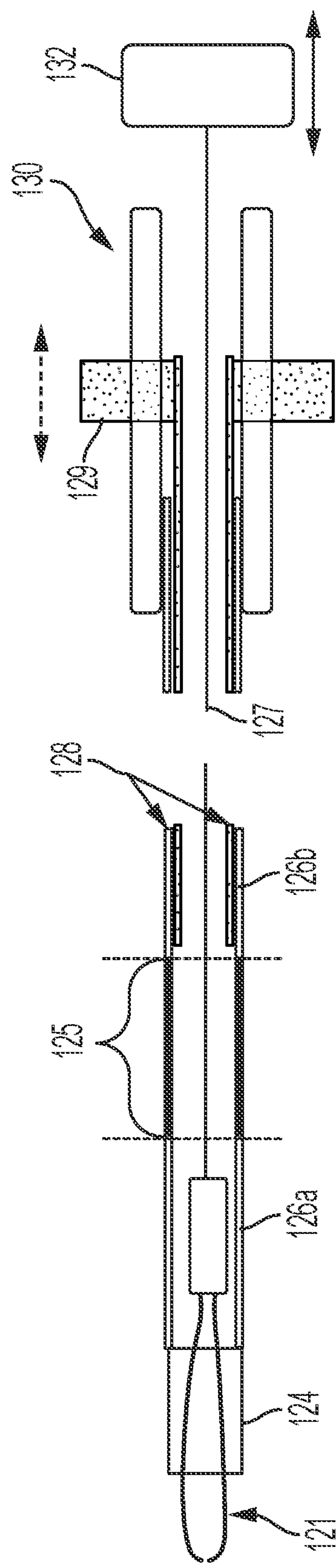
FIGS. 12A and 12B schematically illustrate another implementation of a bendable member in a clip device in which a segmental member can reciprocally move over a bendable member to lock the bendable member from rotating.
Figure 12B:
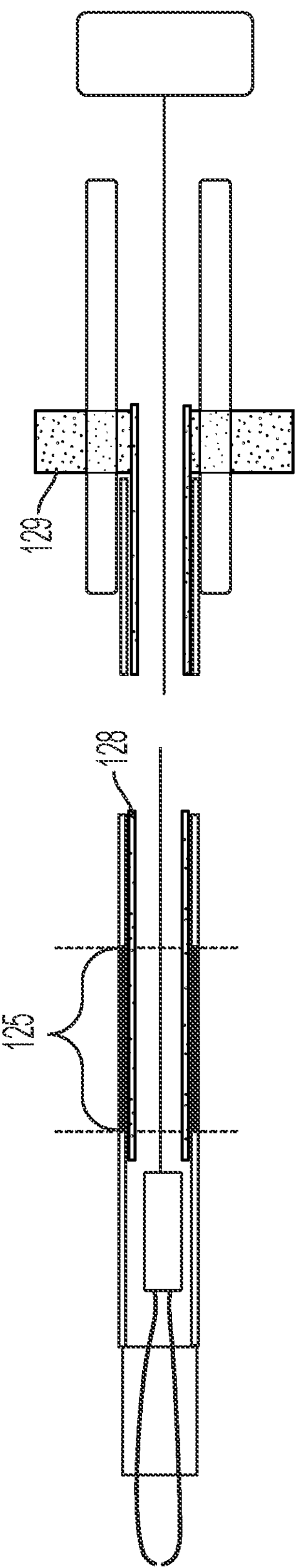

FIGS. 12A and 12B schematically illustrate such an implementation of a clip device with a bendable member in accordance with the present disclosure. As shown in FIGS. 12A and 12B, bendable member 125 can be locked from bending by a rigid segmental member reciprocally movable over the bendable member. In this example, the rigid segmental member is in the form of a tube or inner sheath 128. As further shown in the figures, the device includes a clip 121 having arms with claws, which is shown in a closed state, a pressing pipe 124 connected to an end surface of a distal end region 126*a* of a sheath 126 having a longitudinal channel in which a wire 127 can reciprocally move by operation of a slider 132. A bendable member 125 is connected between distal end region 126*a* and proximal end region 126*b* of the sheath 126 along the longitudinal channel of the sheath.

The bendable member 125 can be in an operational state which allows the bendable member to rotate as shown in FIG. 12A. In the operational state, segmental member 128 does not overlap the bendable member. The segmental member can be operated by a controller, such as a knob 129, connected to a proximal end of the segmental member which can reciprocally move the segmental member over the bendable member. The controller can be on an exterior surface of a handle 130. Operating the controller to move the segmental member over the bendable member 125 as shown in FIG. 12B prevents the bendable member 125 from rotating. When rotation of the bendable member 125 is again desired, operating the controller can move the segmental member 128 away from being in the region of the bendable member 128, for example back to a position as shown in FIG. 12A. The segmental member can be configured to be more rigid than the bendable member by choice of material, design, thickness, etc. or combinations thereof. The segmental member can comprise a metal or polymeric materials such as high density polyethylene, a polyester, a polyetherketone, etc. By this configuration, the bendable member can be locked from rotating until desired by actuating the knobs.

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A clip delivery device, comprising:

a clip having a first arm and second arm, the first arm movable relative to the second arm between an open position and a closed position;

a sheath including a bendable member portion located in a distal end region of the sheath, wherein a longitudinal channel extends within the sheath from a proximal end of the sheath through the bendable member portion; and a wire located within the longitudinal channel of the sheath, wherein a distal end of the wire is connected to a proximal end of the clip, wherein movement of the wire toward the proximal end of the sheath moves the proximal end of the clip toward the bendable member portion, wherein the distal end of the wire extends through a majority portion of the bendable member portion located in the distal end region, wherein the bendable member portion comprises a joint having an articulating distal part and proximal part joined by a pin, and wherein the joint is aligned with the longitudinal channel of the sheath.

2. The clip delivery device of claim 1, wherein the bendable member portion comprises a flexible tube connected to the distal end region of the sheath.

3. The clip delivery device of claim 1, wherein the bendable member portion comprises a flexible tube extending from the distal end region of the sheath.

4. The clip delivery device of claim 1, wherein the sheath further includes a rigid tube portion, wherein the bendable member portion is configured to be more flexible than the rigid tube portion.

5. The clip delivery device of claim 1, wherein the bendable member portion is formed by heat treating a distal end region of the sheath.

6. The clip delivery device of claim 1, wherein the bendable member portion comprises a metal.

7. The clip delivery device of claim 1, wherein the bendable member portion comprises a polymeric material.

8. The clip delivery device of claim 1, further comprising a connection member connecting the proximal end of the clip and the distal end of the wire and slidably movable within the sheath.

9. The clip delivery device of claim 8, wherein a distal end of the bendable member portion does not overlap the distal end of the wire connected to the connection member when the clip is in the closed position.

10. A clip delivery device, comprising:

a clip having a first arm and second arm, the first arm movable relative to the second arm between an open position and a closed position;

a sheath including a bendable member portion located in a distal end region of the sheath, wherein a longitudinal channel extends within the sheath from a proximal end of the sheath through the bendable member portion;

a wire located within the longitudinal channel of the sheath; and a connection member connecting a proximal end of the clip and a distal end of the wire and slidably movable within the sheath, wherein movement of the wire toward the proximal end of the sheath moves the proximal end of the clip toward the bendable member portion, wherein the distal end of the wire extends through a majority portion of the bendable member portion located in the distal end region, and wherein the connection member comprises a joint having an articulating distal part and proximal part joined by a pin.

11. The clip delivery device of claim 8, wherein the connection member can rotate within the bendable member portion.

12. The clip delivery device of claim 8, wherein the connection member has a tapered proximal end connected to the distal end of the wire.

13. The clip delivery device of claim 1, further comprising a segmental member, wherein a distal end of the segmental member is movable between a distal end of the bendable member portion and a proximal end of the bendable member portion to lock the bendable member portion from rotating, and wherein the segmental member is more rigid than the bendable member portion.

14. The clip delivery device of claim 4, further comprising a segmental member, wherein a distal end of the segmental member is movable between a distal end of the bendable member portion and a proximal end of the bendable member portion to lock the bendable member from rotating, and wherein the segmental member is more rigid than the bendable member portion.

15. The clip delivery device of claim 8, further comprising a segmental member, wherein a distal end of the segmental member is movable between a distal end of the bendable member portion and a proximal end of the bendable member portion to lock the bendable member from rotating, and wherein the segmental member is more rigid than the bendable member portion.

16. The clip delivery device of claim 4, wherein the bendable member portion is located distal to the rigid tube portion.

17. The clip delivery device according to claim 1, wherein the distal end of the wire extends through an entire length of the bendable member portion located in the distal end region.

18. The clip delivery device according to claim 4, wherein the rigid tube portion is a first rigid tube portion and the sheath further includes a second rigid tube portion connected to a proximal end of the bendable member portion, wherein the bendable member portion is more flexible than the second rigid tube portion, and wherein the longitudinal channel further extends through the second rigid tube portion.

19. The clip delivery device according to claim 1, further including a pressing pipe connected to a distal end of the bendable member portion, wherein the longitudinal channel further extends through the pressing pipe.

* * * * *